United States Patent [19]

Ikegami et al.

[11] 4,200,751

[45] Apr. 29, 1980

[54] LACTONES OF QUINOLINE CARBOXYLIC ACIDS

[75] Inventors: Seiji Ikegami; Yoshihiro Hatano, both of Osaka, Japan

[73] Assignee: Yamamoto Kagaku Gosei Co., Ltd., Osaka, Japan

[21] Appl. No.: 853,781

[22] Filed: Nov. 21, 1977

Related U.S. Application Data

[63] Continuation of Ser. No. 706,088, Jul. 16, 1976, abandoned.

[30] Foreign Application Priority Data

Aug. 6, 1975 [JP] Japan .................................. 50-94950

[51] Int. Cl.$^2$ ............................................ C07D 491/14

[52] U.S. Cl. ........................................ 546/89; 544/14; 544/126; 544/361; 544/344; 546/170; 8/1 B

[58] Field of Search ..................... 260/287 CF, 287 L; 546/89

[56] References Cited

U.S. PATENT DOCUMENTS 3,931,228 1/1976 Borror .......................... 260/287 CF

FOREIGN PATENT DOCUMENTS 1389716 11/1972 United Kingdom .

*Primary Examiner*—Donald G. Daus
*Assistant Examiner*—David E. Wheeler
*Attorney, Agent, or Firm*—E. Frank McKinney; Paul S. Phillips, Jr.

[57] ABSTRACT

Lactone electron donative color-forming agents of quinoline-carboxylic acid are disclosed having the general formulae (I) and (II)

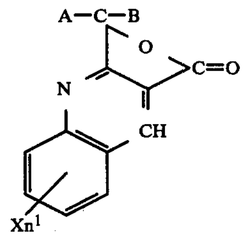

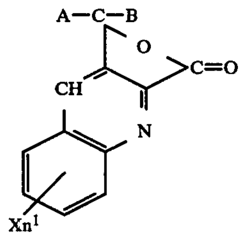

wherein A and B represent a variety of chemical moieties, X represents halo- or nitro- and $n^1$ is an integer of 0–4. The color-forming agents are useful in recording materials of the pressure-sensitive and heat-sensitive varieties, and the like.

3 Claims, No Drawings

LACTONES OF QUINOLINE CARBOXYLIC ACIDS

This is a continuation of application Ser. No. 706,088, filed July 16, 1976 now abandoned.

This invention relates to novel lactone compounds of quinoline carboxylic acid represented by the undermentioned general formula (I) and/or (II) and recording materials utilizing said compounds as electron donative color-forming material.

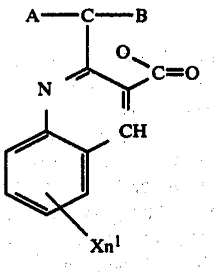
(I)

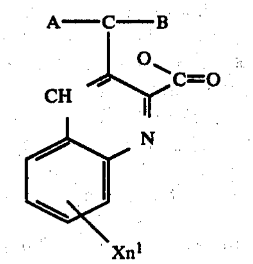
(II)

wherein A and B represent the same or different as shown below; X represents halo- or nitro-; and $n^1$ is an integer of 0–4.

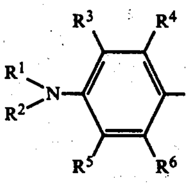
,
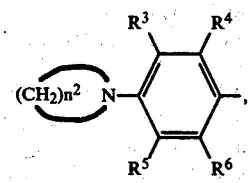
,
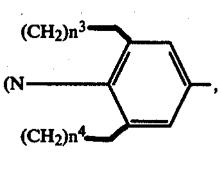
,
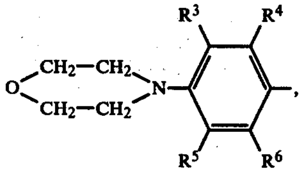
,
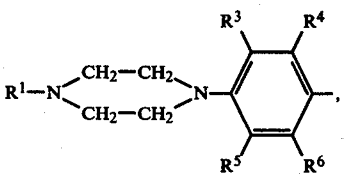
,
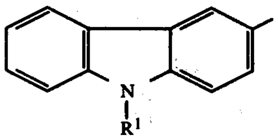
,

-continued

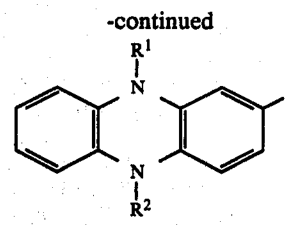
,
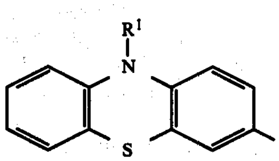
,
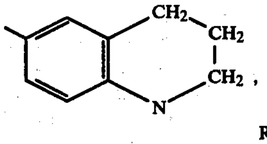
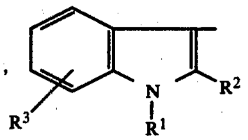
,
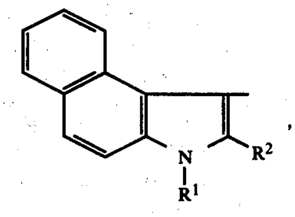
,
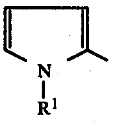
,
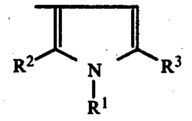
,
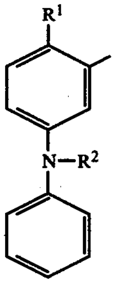

wherein $R^1$ and $R^2$ are hydrogen, alkyl which may also be substituted, alicyclic which may also be substituted, phenyl which may also be substituted, or benzyl which may also be substituted; $R^3$, $R^4$, $R^5$, and $R^6$ are hydrogen, halogen, alkyl which may also be substituted, alkoxy which may also be substituted, alicyclic which may also be substituted, phenyl which may also be substituted, benzyl which may also be substituted, benzyloxy which may also be substituted or dialkylamino; $n^2$ is 4 or 5; and $n^3$ and $n^4$ are respectively 2 or 3.

The lactone compounds of quinoline carboxylic acid represented by the above described general formulae (I) and (II) are synthetic compounds obtained by the present inventors, and although they themselves are usually faintly colored crystals they are characterized by that when their solutions dissolved in an organic solvent are brought in contact with an electron receptive color-developing agent (hereinafter abbreviated color-developing agent) such as active clay or phenolic-resin, the lactone ring in said compounds opens and immediately produces green, blue, or purplish-blue color. They are therefore very useful as electron donative color-forming agents (hereinafter abbreviated color-forming agents) for the manufacture of recording materials.

As is well known, recording materials utilizing color-forming agents include pressure-sensitive recording paper, heat-sensitive recording paper, electrothermal recording paper, hectograph transfer paper, and the like. Lactone compounds are generally used as color-forming agents and lactone compounds having various hues have been invented. At present, however, Crystal Violet Lactone (CVL) is in almost exclusive use as a blue color-forming agent. CVL exhibits rapid color development but; it has often been pointed out that CVL is deficient, in that the color fastness such as against light, water and the like is low after the color-forming. That is to say, when use is made of active clay as color-developing agent the color-forming substance is immediately decolorized in contact with water. Also, when use is made of phenol resin as color-developing agent, no decolorization due to water takes place; but several days of exposure to sun light results in almost complete decolorization. Therefore, development of blue color-forming agent which is rapid in the color development and yet possesses water-fastness as well as light-fastness after color-forming, is being keenly desired.

During the course of the investigation which was carried out to solve this problem, it was discovered that the compounds represented by the general formulae (I) and (II), lactone compounds of quinoline-carboxylic acid, are useful as the color-forming agents, most of which develop bluish color. That the compounds are rapid in the color development and possess good water-fastness as well as good light-fastness after the color-forming. Also, the color-forming agents represented by the general formulae (I) and (II) which are developed red to reddish purple, are very useful in practice because of good resistance to decolorization in contact with water and even upon exposure to sunlight.

The lactone compounds of quinolinecarboxylic acid represented by the general formula (I) can usually be synthesized in the following two ways.

(i) The case where A and B are of the same structure (that is, A=B)

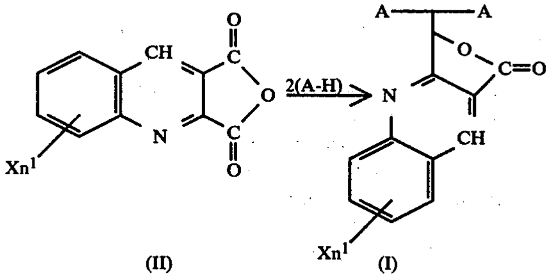

(II) (I)

-continued and

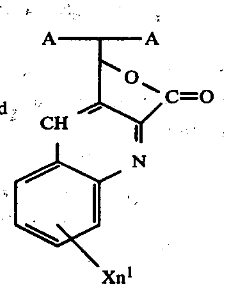

(II)

One mole of quinoline-2,3-dicarboxylic acid anhydride (II) and 2 moles of (A - H) (usually it is preferable to use in somewhat excess) are allowed to react either in a dehydration condensing agent or along with a dehydration condensing agent in the presence of a Lewis acid catalyst, either in an inert solvent or without solvent. As dehydration condensing agents, use can be made of lower fatty acid anhydrides such as acetic acid anhydride, propionic acid anhydride, and the like, phosphorus oxychloride, phosphorus trichloride, and inorganic acids such as sulfuric acid, polyphosphoric acid, and the like. As Lewis acid catalysts, use can be made of $AlCl_3$, $ZnCl_2$, $SnCl_4$, $FeCl_3$, and the like. Also, as inert solvents, use can be made of chloroform, carbon tetrachloride, dichloroethane, trichloroethane, tetrachloroethane, trichloroethylene, benzene, toluene, xylene, and the like.

(ii) The case where A and B differ in the structure:

When 1 mole of quinoline-2,3-dicarboxylic acid anhydride (II) and 1 mole of (A - H) or 1 mole of (B - H) are either heated in a solvent or without solvent, or subjected to Friedel-Crafts reaction by the aid of a Lewis acid catalyst, keto-acid of (IV - a) and/or (IV - a′) or (IV - b) and/or (IV - b′) are obtained Formula IV is found in the paragraph next below. Then 1 mole of keto-acid of (IV - a) and/or (IV - a′) or (IV - b) and/or (IV - b′) and 1 mole of (B - H) or (A - H) are allowed to react in a dehydration condensing agent. Use can be made of the same dehydration condensing agents, Lewis acids and inert solvent as the above-described case (i). It is understood that this method is applicable also to the case where A and B are of the same structure.

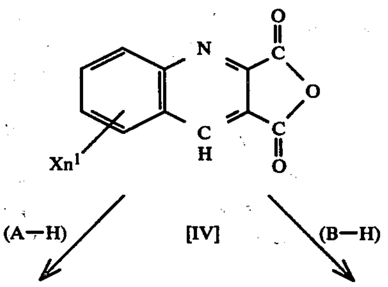

[IV]

-continued

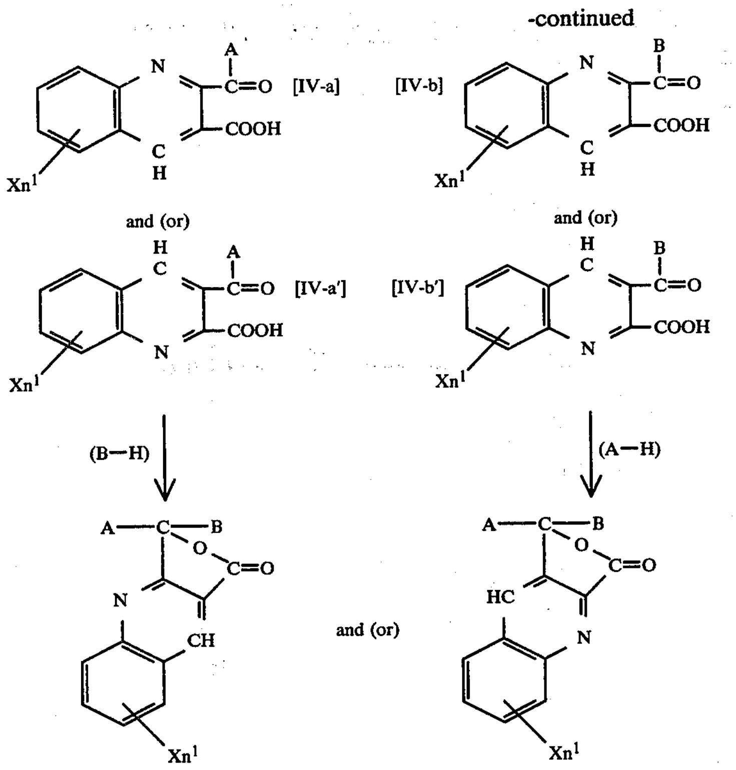

The lactone compounds of quinoline-carboxylic acid (I) and (II) are in the relation of isomers, and the lactone compounds of quinoline-carboxylic acid obtained in accordance with the above-described process are usually obtainable as a mixture of isomers, but sometimes also singly either as (I) or (II). These mixtures of isomers can be easily separated into the respective components by column chromatography, and the like; but, as the hues of these isomers resemble each other in use as the color formers of the recording material, the use of a mixture, as such, is not objectionable.

Table 1 shows concrete examples of lactone compounds of quinoline-carboxylic acid represented by the general formulae (I) and (II) obtained in accordance with the above-described methods, which compounds are rapid in color development and excellent in water-fastness as well as light-fastness. Each compound is disclosed together with the hue that it develops. The listed hues are those which are seen after color-forming occurs on silica gel with respect to the solutions of the respective compounds.

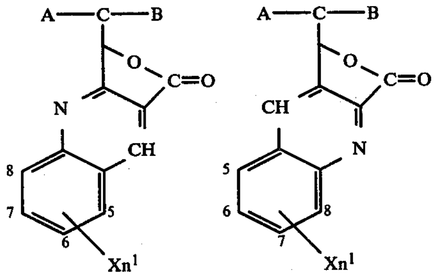

| Compound | A | B | $Xn^1$ | Color |
|---|---|---|---|---|
| (1) | 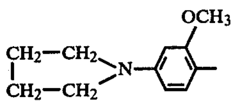 | 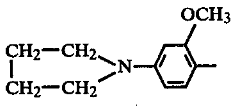 | — | green |
| (2) | 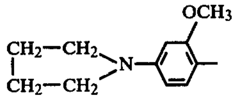 | 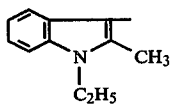 | — | blue |

-continued
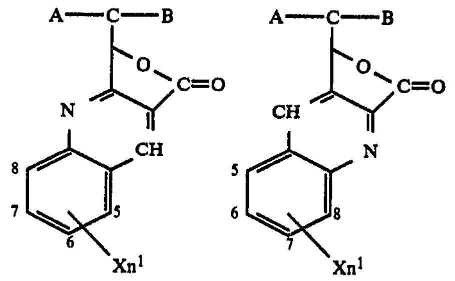
| Compound | A | B | $Xn^1$ | Color |
|---|---|---|---|---|
| (3) | 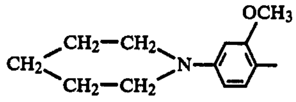 | 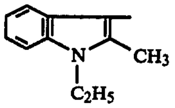 | — | blue |
| (4) | 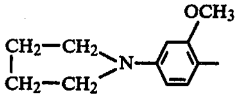 | 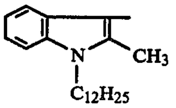 | — | blue |
| (5) | 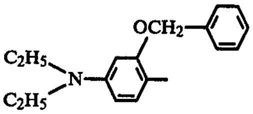 | 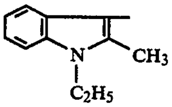 | — | blue |
| (6) | 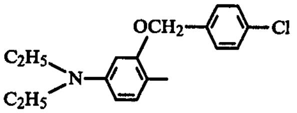 | 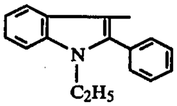 | — | blue |
| (7) | 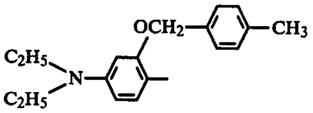 | 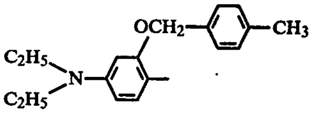 | — | blue-green |
| (8) | 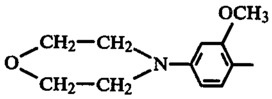 | 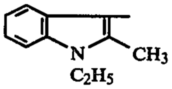 | — | blue |
| (9) | 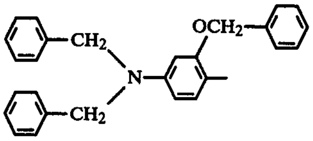 | 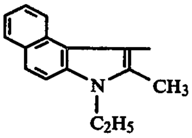 | — | blue |
| (10) | 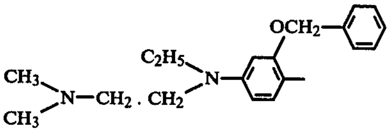 | 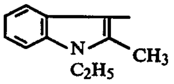 | — | green |
| (11) | 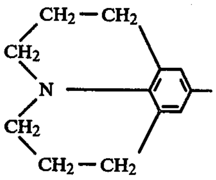 | 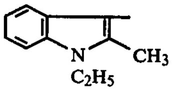 | — | blue |

-continued
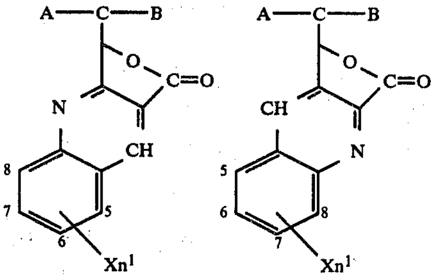
| Compound | A | B | $Xn^1$ | Color |
|---|---|---|---|---|
| (12) | 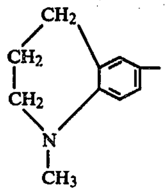 | 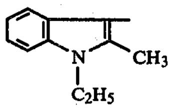 | — | blue |
| (13) | 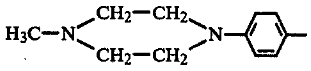 | 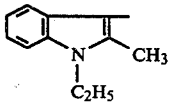 | — | purple-blue |
| (14) | 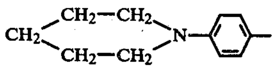 | 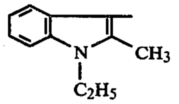 | — | blue |
| (15) | 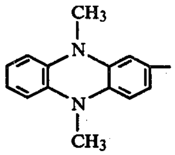 | 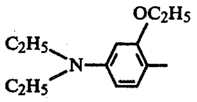 | — | blue |
| (16) | 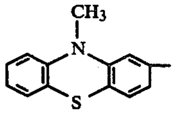 | 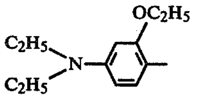 | — | blue |
| (17) | 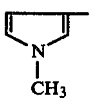 | 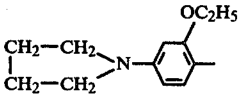 | — | green |
| (18) | 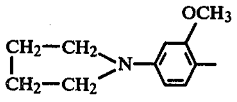 | 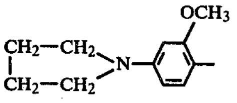 | 6 or 7-Cl | green |
| (19) | 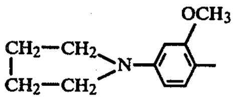 | 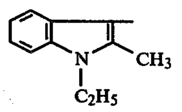 | 6,7-$Cl_2$ | blue |
| (20) | 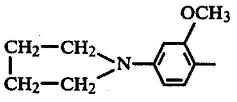 | 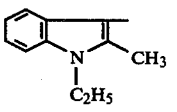 | 6 or 7-$NO_2$ | blue |

-continued
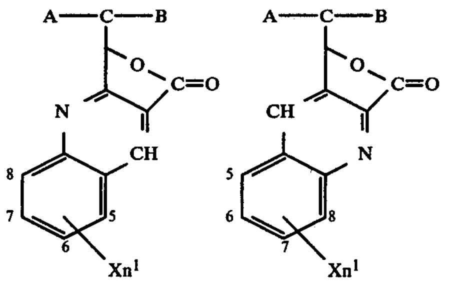
| Compound | A | B | $Xn^1$ | Color |
|---|---|---|---|---|
| (21) | 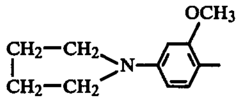 | 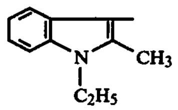 | 6,7-$(NO_2)_2$ | blue |
| (22) | 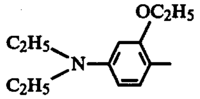 | 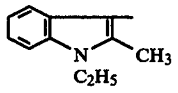 | — | blue |
| (23) | 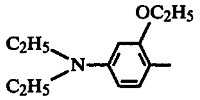 | 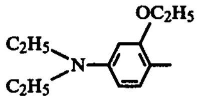 | — | green |
| (24) | 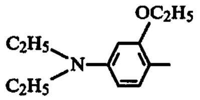 | 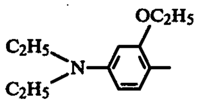 | 6 or 7-Cl | green |
| (25) | 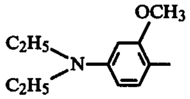 | 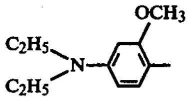 | 6 or 7-$NO_2$ | green |
| (26) | 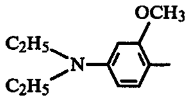 | 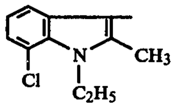 | — | blue |
| (27) | 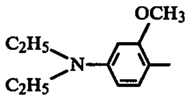 | 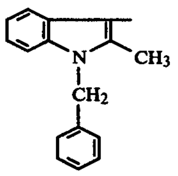 | — | blue |
| (28) | 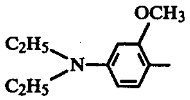 | 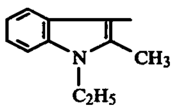 | — | blue |
| (29) | 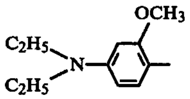 | 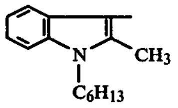 | — | blue |
| (30) | 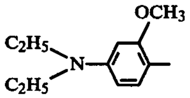 | 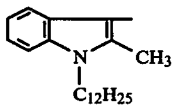 | — | blue |

-continued
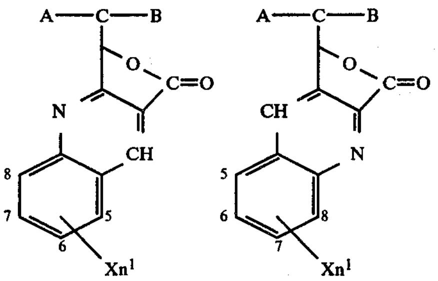
| Compound | A | B | Xn[1] | Color |
|---|---|---|---|---|
| (31) | 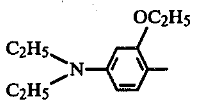 | 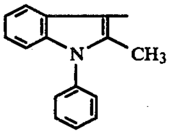 | — | blue |
| (32) | 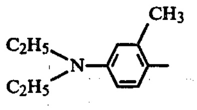 | 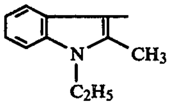 | — | green |
| (33) | 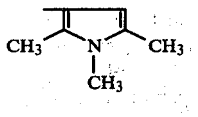 | 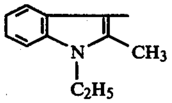 | — | red |
| (34) | 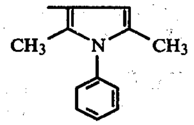 | 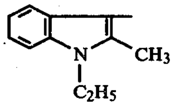 | — | red |
| (35) | 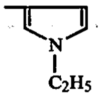 | 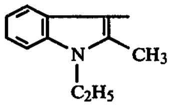 | — | red |
| (36) | 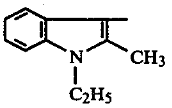 | 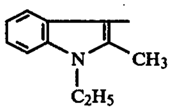 | — | reddish-purple |
| (37) | 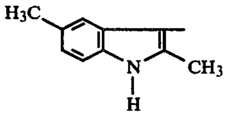 | 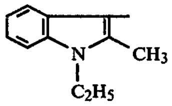 | — | red |
| (38) | 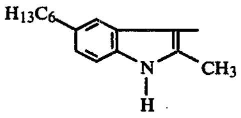 | 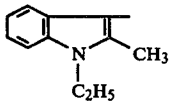 | — | red |
| (39) | 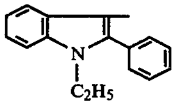 | 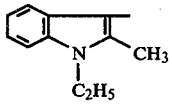 | — | reddish-purple |

-continued

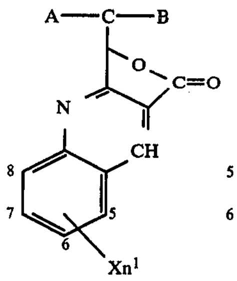
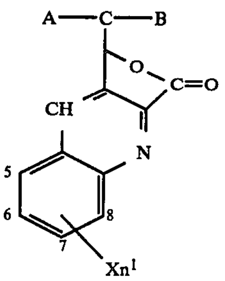

| Compound | A | B | $Xn^1$ | Color |
|---|---|---|---|---|
| (40) | 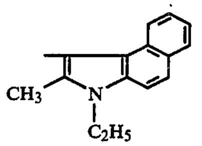 | 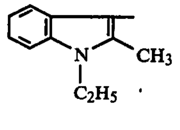 | — | reddish-purple |
| (41) | 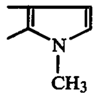 | 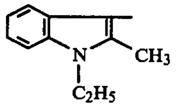 | — | red |

The substituents that are substituted in each of $R^1$, $R^2$, $R^3$, $R^4$, $R^5$, and $R^6$ include halogen, cyano, alkoxy, alkylamino, or polyfluoromethyl, and the like; and, even when these substituents are present in the above described radicals, the synthetic products possess the characteristics of the lactone compounds of this invention without causing any hindrance in the synthetic reaction.

The synthetic examples of representative compounds in Table 1 will be shown below.

SYNTHESIS EXAMPLE 1

Preparation of 2,2-bis(4-pyrrolidino-2-methoxyphenyl)-2H,5H-5-oxofurano[3,4,b]quinoline (V) and 2,2-bis(4-pyrrolidino-2-methoxyphenyl)-2H,5H-5-oxofurano[4,3,b]quinoline (VI); (Compound No. 1)

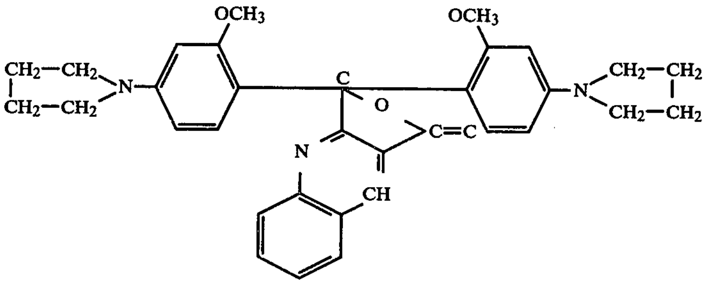

(V)

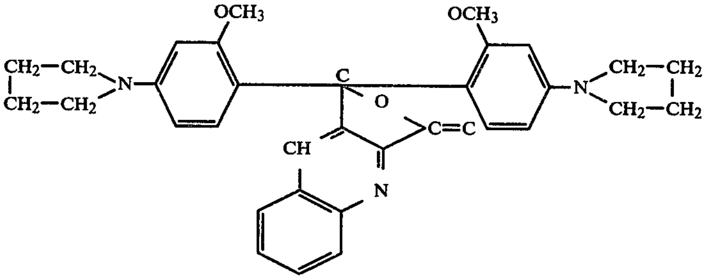

(VI)

1.8 g of 4-pyrrolidinoanisole, 1 g of quinoline 2,3-dicarboxylic acid anhydride, and 20 ml. of acetic anhydride are allowed, to react at 50°-60° C. for 1 hour, and then 100 ml. of toluene and 50 ml. of 25% ammonia water are added. After one hour of heating at reflux temperature the toluene layer is separated and concentrated which gives 1.6 g (59.5% of theoretical yield) of a mixture of 2,2-bis(4-pyrrolidino-2-methoxyphenyl)-2H,5H-5-oxofurano[3,4,b]quinoline (V) and 2,2-bis(4-pyrrolidino-2-methoxyphenyl)-2H,5H-5-oxofurano[4,3,b]quinoline (VI), pale brown crystals, m.p. 196°-198° C.

By the following analysis, it was confirmed that the molecular formula of this compound is $C_{33}H_{33}N_3O_4$.

| | C | H | N |
|---|---|---|---|
| Theoretical value | 73.98 | 6.22 | 7.85 |

-continued

| | C | H | N |
|---|---|---|---|
| Observed value | 73.93 | 6.21 | 7.82 |

SYNTHESIS EXAMPLE 2

Preparation of 2-1ethyl-2-methylindol-3-yl-2-(4-pyrrolidino-2-methoxyphenyl)-2H,5H-5-oxofurano[3,4,b-]quinoline (VII) and 2-(1-ethyl-2-methylindol-3-yl)-2-(4-pyrrolidino-2-methoxyphenyl)-2H,5H-5-oxofurano[4,3,b]quinoline (VIII); (Compound No. 2)

ammonia water is added to decompose the acetic anhydride. Upon concentration after extraction with 100 ml of toluene, there is obtained 2.3 g (79.3% of theoretical yield) of a mixture of 2-(1-ethyl-2-methylindol-3-yl)-2-(4-pyrrolidino-2-methoxyphenyl)-2H,5H-5-oxofurano[3,4,b]quinoline (VII) and 2-(1-ethyl-2-methylindol-3-yl)-2-(4-pyrrolidino-2-methoxyphenyl)-2H,5H-5-oxofurano[4,3,b]quinoline (VIII). Pale yellow-green crystals, m.p. 252°-253° C.

By the following analysis it was confirmed that the molecular formula of this compound is $C_{33}H_{31}N_3O_3$.

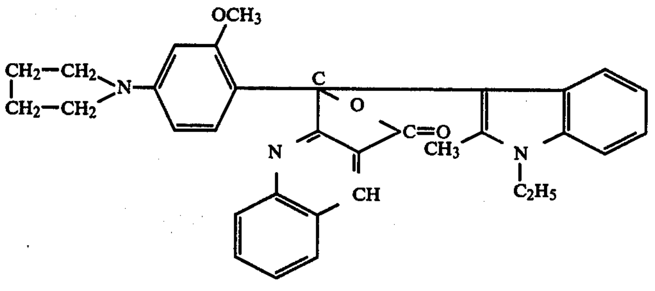

(VII)

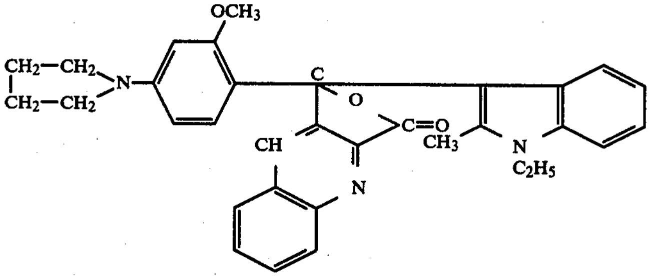

(VIII)

10.5 g of 1-ethyl-2-methylindole, 13.2 g of quinoline-2,3-dicarboxylic acid anhydride and 20 ml of xylene are allowed to react under reflux for 5 hours. Then 70 ml of 25% ammonia water is added to dissolve the contents, and unreacted indole is removed by extraction with a small amount of toluene. by acidifying the ammonia water solution there is obtained 12.2 g (51.7% of theoretical yield) of crude mixture of 2-(1-ethyl-2-methylindol-3-yl)carbonylquinoline-3-carboxylic acid and 3-(1-ethyl-2-methylindol-3-yl)carbonylquinoline-2-carboxylic acid. Pale pink crystals, m.p. 196°-198° C.

Next, 2 g of keto acid, 1 g of 3-pyrrolidinoanisole, and 20 ml of acetic anhydride are allowed to react at 50°-60° C. for 3 hours, and thereafter 50 ml of 25%

| | C | H | N |
|---|---|---|---|
| Theoretical value | 76.56 | 6.05 | 8.12 |
| Observed value | 76.65 | 6.05 | 8.10 |

SYNTHESIS EXAMPLE 3

Preparation of 2-(1-ethyl-2-methylindol-3-yl)-2-(4-piperidino-2-methoxyphenyl)-2H,5H-5-oxofurano[3,4,b]quinoline (IX) and 2-(1-ethyl-2-methylindol-3-yl)-2-(4-piperidino-2-methoxyphenyl)-2H,5H-5-oxofurano[4,3,b]quinoline (X); (Compound No. 3)

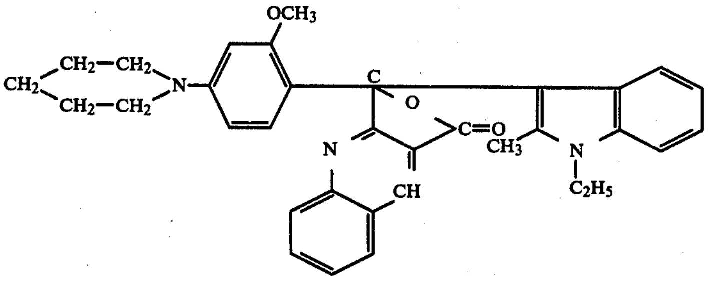

(IX)

-continued

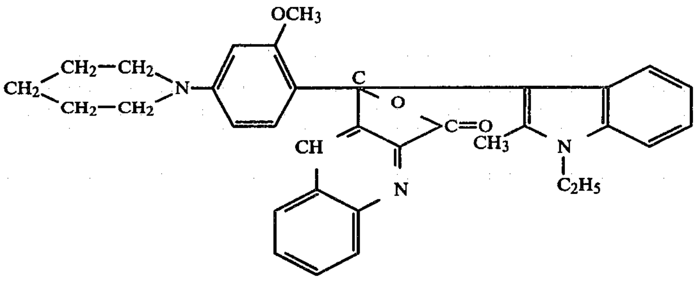

Two grams of the keto acid from the synthesis of Example 2, 1.1 g of 3-piperidinoanisole and 30 ml of acetic anhydride are allowed to react at 50°-60° C. for 3 hours and then 50 ml of 25% ammonia water and 100 ml of toluene are added and heated at reflux temperature for 1 hour. By separating the toluene layer, followed by concentrating, there is obtained 2.1 g (70.0% of theoretical yield) of mixture of 2-(1-ethyl-2-methylindol-3-yl)-2-(4-piperidino-2-methoxyphenyl)-2H,5H-5-oxofurano[3,4,b]quinoline (IX) and 2-(1-ethyl-2-methylindol-3-yl)-2-(4-piperidino-2-methoxyphenyl)-2H,5H-5-oxofurano[4,3,b]quinoline (X). Pale yellow crystals, m.p. 212°-214° C.

By the following analysis it was confirmed that the molecular formula of this compound is $C_{34}H_{33}N_3O_3$.

| | C | H | N |
|---|---|---|---|
| Theoretical value | 76.80 | 6.27 | 7.90 |
| Observed value | 76.75 | 6.25 | 7.88 |

SYNTHESIS EXAMPLE 4

Preparation of 2-(1-ethyl-2-methylindol-3-yl)-2-(4-diethylamino-2-benzyloxyphenyl)-2H,5H-5-oxofurano[3,4,b]quinoline (XI) and 2-(1-ethyl-2-methylindol-3-yl)-2-(4-diethylamino-2-benzyloxyphenyl)-2H,5H-5-oxofurano[4,3,b]quinoline (XII); (Compound No. 5)

(XI)

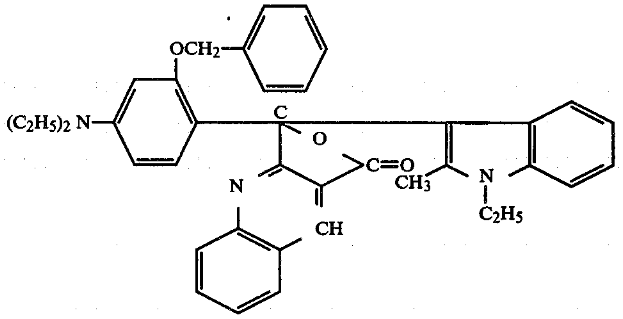

(XII)

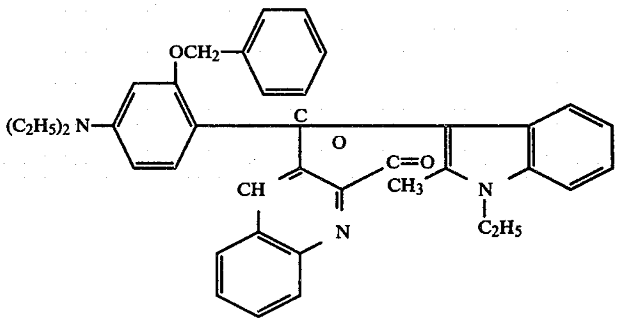

Two grams of the keto acid from the synthesis of Example 2, 1.4 g of 3-diethylamine-benzyloxybenzene, and 20 ml of acetic anhydride are allowed to react at 50°-60° C. for 4 hours. Then, by the same treatment as in Synthesis Example 3, there is obtained 2.6 g (78.9% of theoretical yield) of a mixture of 2-(1-ethyl-2-methylindol-3-yl)-2-(4-diethylamino-2-benzyloxyphenyl)-2H,5H-5-oxofurano[3,4,b]quinoline (XI) and 2-(1-ethyl-2-methylindol-3-yl)-2-(4-diethylamino-2-benzyloxyphenyl)-2H,5H-5-oxofurano[4,3,b]quinoline (XII). Pale yellow crystals, m.p. 183°-184° C.

By the following analysis it was confirmed that the molecular formula of this compound is $C_{39}H_{37}N_3O_3$.

| | C | H | N |
|---|---|---|---|
| Theoretical value | 78.62 | 6.27 | 7.05 |
| Observed value | 78.69 | 6.25 | 7.00 |

SYNTHESIS EXAMPLE 5

Preparation of 2-(1-ethyl-2-methylindol-3-yl)-2-(4-morpholine-2-methoxyphenyl)-2H,5H-5-oxofurano[3,4,b]quinoline (XIII) and 2-(1-ethyl-2-methylindol-3-yl)-2-(4-morpholine-2-methoxyphenyl)-

2H,5H-5-oxofurano[4,3,b]quinoline (XIV); (Compound No. 8)

-continued (XIII)

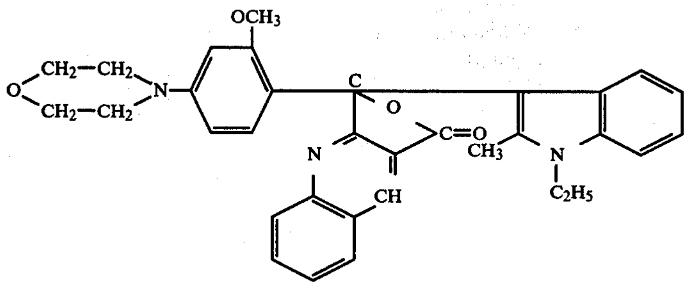

(XIV)

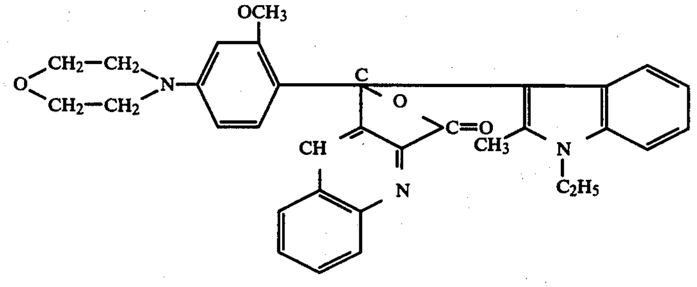

Two grams of the keto acid from the synthesis of Example 2, 1.1 g of 3-morpholinoanisole, and 20 ml of acetic anhydride are allowed to react at 50°-60° C. for 2 hours; and the same treatment as in Synthesis Example 3 yields 2.0 g (66.7% of theoretical yield) of a mixture of 2-(1-ethyl-2-methylindol-3-yl)-2-(4-morpholine-2-methoxyphenyl)-2H,5H-5-oxofurano[3,4,b]quinoline (XIII) and 2-(1-ethyl-2-methylindol-3-yl)-2-(4-morpholine-2-methoxyphenyl)-2H,5H-5-oxofurano[4,3,b-]quinoline (XIV). Pale yellow crystals, m.p. 243°-244° C.

By the following analysis it was confirmed that the molecular formula of this compound is $C_{33}H_{31}N_3O_4$.

| | C | H | N |
|---|---|---|---|
| Theoretical value | 74.26 | 5.87 | 7.88 |
| Observed value | 74.21 | 5.89 | 7.85 |

SYNTHESIS EXAMPLE 6

Preparation of 2-(1-ethyl-2-methylindol-3-yl)-2-(4-diethylamine-2-ethoxyphenyl)-2H,5H-5-oxofurano[3,4,b]quinoline (XV) and 2-(1-ethyl-2-methylindol-3-yl)-2-(4-diethylamino-2-ethoxyphenyl)-2H,5H-5-oxofurano[4,3,b]quinoline (XVI); (Compound No. 22)

(XV)

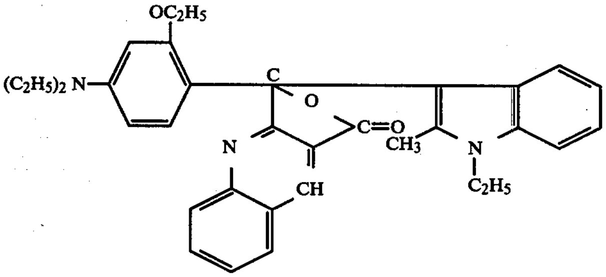

(XVI)

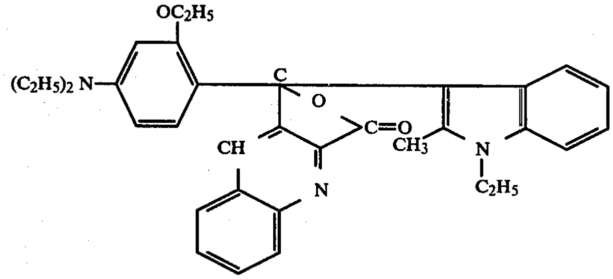

Two grams of the keto acid from the synthesis of Example 2, 1.1 g of 4-diethylamino-2-ethoxybenzene and 20 ml of acetic anhydride have been allowed to react at 50°-60° C. for 1 hour. Then, by the same treatment as in Synthesis Example 3, there is obtained 2.4 g (80.0% of theoretical yield) of a mixture of 2-(1-ethyl-2-methylindol-3-yl)-2-(4-diethylamine-2-ethoxyphenyl)-

2H,5H-5-oxofurano[3,4,b]quinoline (XV) and 2-(1-ethyl-2-methylindol-3-yl)-2-(4-diethylamine-2-ethoxyphenyl)-2H,5H-5-oxofurano[4,3,b]quinoline (XVI). Pale yellow crystals, m.p. 280°-281° C.

By the following analysis it was confirmed that the molecular formula of this compound is $C_{34}H_{35}N_3O_3$.

| | C | H | N |
|---|---|---|---|
| Theoretical value | 76.51 | 6.62 | 7.87 |
| Observed value | 76.47 | 6.60 | 7.88 |

In order to prepare pressure-sensitive recording paper from the color-forming agent, the lactone compounds represented by the general formula (I) and (II) obtained in this way, use may be made of the prior known method (for example, as disclosed in Japanese Patent Publication No. 4,614/1971). That is to say, one or moe of the lactone compounds represented by the general formula (I) and (II) are dissolved in a low volatile solvent such as alkyldiphenyl, alkylnaphthalene, and the like, and according to the method known, per se, the solution is sealed in microcapsules of aqueous solution of gelatine-gum arabic. The pressure-sensitive recording paper is prepared by applying the aqueous dispersion onto the under surface of the upper leaf and the color-developing agent onto the upper surface of the under leaf. When this recording paper is locally pressed, the capsules in the pressed portion rupture and the color-forming agent in the capsules is absorbed by the color-developing agent on the upper surface of the under leaf, thereby color being developed, and thus the object of the recording is achieved.

The preparation of heat-sensitive recording paper may also be resorted to the prior known method (for example, as disclosed in Japanese Patent Publication No. 14,039/1970). That is to say, the color-forming agent, the lactone compound represented by the general formula (I) and (II), and the color-developing agent such as bisphenol A are respectively triturated with an aqueous solution of a binding agent such as polyvinyl alcohol, and the like and then mixed. The resulting mixture is applied onto a support such as paper or the like and dried. When the heat-sensitive recording paper prepared in this way is locally heated with a heat pen or a heat head the color-forming agent and the color-developing agent in the heated portion melt and react to result in color-development, and thus the object of the recording can be achieved.

Next, this invention will be explained with reference to some examples.

EXAMPLE 1

0.3 g of lactone compound, Compound No. 1, is dissolved in 12 g of alkylnaphthalene KMCR (Trade name of Kureha Kagaku) as solvent, and the resulting solution is emulsified together with 25 ml of water containing 3.25 g of gum arabic at 50° C. Then, after 25 ml of water containing 3.25 g of gelatin has further been added so as to complete emulsification pH is adjusted to 4 by addition of acetic acid. In this case, a liquid film consisting of gelatine-gum arabic is formed around the oil drops containing the lactone compound. After adding 50 ml of water the emulsion is cooled below 10° C. In order to harden the film 1 ml of formalin is added, and thereafter a 10% aqueous solution of sodium hydroxide is added until pH 9-10, and temperature is slowly returned to room temperature. The thus obtained suspension is applied onto the under surface of the upper leaf and dried. On the other hand the color-developing agent is applied onto the upper surface of the under leaf.

When copied using the upper leaf and the under leaf prepared as above described a bluish green color is quickly developed if use is made of active clay as color-developing agent, while a green color is quickly developed if use is made of phenolic compound. The thus developed image is excellent in water-fastness as well as light-fastness.

EXAMPLE 2

0.3 g of lactone compound, Compound No. 2 is dissolved in 12 g of alkylnaphthalene KMCR (Trade name by Kureha Kagaku) as solvent and by the same treatment as Example 1 an aqueous dispersion of microcapsules is obtained. This is spray-dried to give a powder of microcapsules, which is mixed in a 4% xylene solution of p-phenylphenol-formaldehyde condensate to form a dispersion. The dispersion is next coated on paper and dried. When this coated sheet is locally pressed, a blue color is quickly developed, and the thus-developed image is excellent in water-fastness as well as light-fastness.

EXAMPLE 3

0.5 g of lactone compound, Compound No. 3 is added to a mixture of carnauba wax 10 g, dibutylphthalate 5 g, polyethylene glycol octylphenyl ether 0.1 g (80°-90° C.) and dissolved. The resulting product is applied onto the under surface of the upper leaf. On the other hand, the color-developing agent is applied onto the upper surface of the under leaf. When copied using the upper leaf and the under leaf prepared as above described a blue color is quickly developed in either of active clay under leaf or phenolic compound under leaf, and the thus copied image is excellent in water-fastness as well as light-fastness.

EXAMPLE 4

3.5 g of lactone compound, Compound No. 5, 15 g of 10% aqueous solution of polyvinyl alcohol, and 6.5 g of water are ground together for 24 hours (A component). On the other hand, 35 g of bisphenol A, 150 g of 10% aqueous solution of polyvinyl alcohol, and 65 g of water are ground together for 24 hours (B component).

Then 3 parts by weight A component and 67 parts by weight of B component are mixed to form a dispersion, which is applied onto paper.

When the heat-sensitive recording paper prepared as above described is locally heated with a heat pen or a heat head a blue color is quickly developed. The developed image is excellent in water-fastness as well as light-fastness.

EXAMPLE 5

3.5 g of lactone compound, Compound No. 8, 15 g of 10% aqueous solution of polyvinyl alcohol, and 6.5 g of water are ground together for 24 hours (A component). Then 35 g of bisphenol A, 150 g of 10% aqueous solution of polyvinyl alcohol, and 65 g of water are ground together for 24 hours (B component). Further 100 g of cuprous iodine, 75 g of 10% aqueous solution of polyvinyl alcohol, and 25 g of water are ground together for 24 hours (C component). 3 g of A component, 67 g of B component, and 200 g of C component prepared as above are mixed to form a dispersion, which is applied onto paper.

When the thus prepaed electroheat-sensitive recording paper is scanned with the appliance of AC voltage a blue color is quickly developed, and the developed image is excellent in water-fastness as well as light-fastness.

What is claimed is:

1. A compound represented by

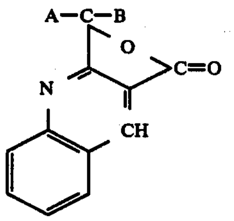

-continued

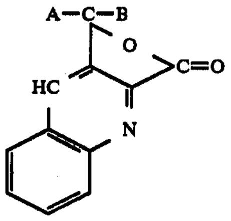

wherein A is

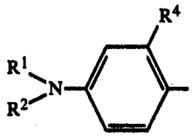

and B is

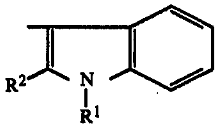

;

and wherein $R^1$ and $R^2$ are alkyl groups of 1 to 4 carbon atoms and $R^4$ is an alkoxy group of 1 to 4 carbon atoms.

2. A compound of claim 1 wherein the alkyl and alkoxy groups contain 1–2 carbon atoms.

3. A compound of claim 2 wherein A is

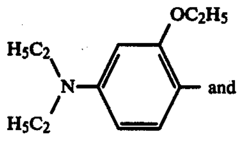

and B is

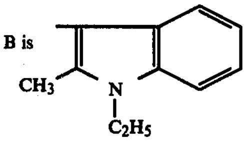

.

* * * * *

UNITED STATES PATENT AND TRADEMARK OFFICE

CERTIFICATE OF CORRECTION

PATENT NO. : 4,200,751

DATED : April 29, 1980

INVENTOR(S) : Seiji Ikegami et al.

It is certified that error appears in the above—identified patent and that said Letters Patent is hereby corrected as shown below:

Column 1, line 15, formula (I), change

" 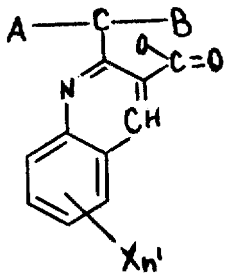 " to — 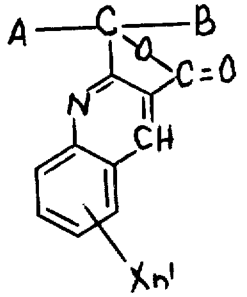 —

Column 1, line 25, formula (II), change

" 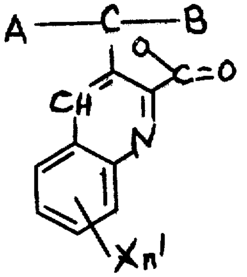 " to — 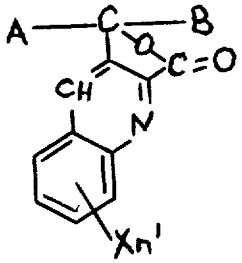 —

UNITED STATES PATENT AND TRADEMARK OFFICE

CERTIFICATE OF CORRECTION

PATENT NO. : 4,200,751

DATED : April 29, 1980

INVENTOR(S) : Seiji Ikegami et al.

It is certified that error appears in the above—identified patent and that said Letters Patent is hereby corrected as shown below:

Column 2, line 20, change

" 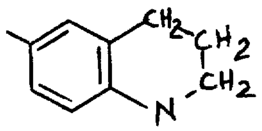 " to — 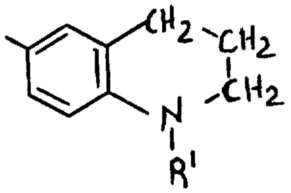 —

Column 9, Compound (16), change

" 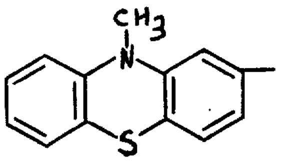 " to — 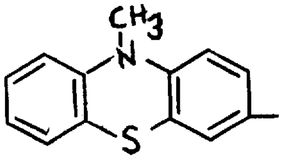 —

UNITED STATES PATENT AND TRADEMARK OFFICE
CERTIFICATE OF CORRECTION

PATENT NO. : 4,200,751

DATED : April 29, 1980

INVENTOR(S) : Seiji Ikegami et al.

It is certified that error appears in the above—identified patent and that said Letters Patent is hereby corrected as shown below:

Column 15, Compound (41), change

" 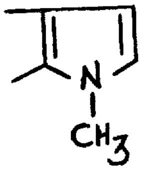 " to — 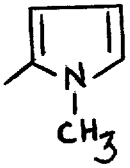 —

Signed and Sealed this

*Fifth* Day of *August 1980*

[SEAL]

*Attest:*

SIDNEY A. DIAMOND

*Attesting Officer* *Commissioner of Patents and Trademarks*